United States Patent
Kim et al.

(10) Patent No.: US 9,271,833 B2
(45) Date of Patent: Mar. 1, 2016

(54) TRANSCATHETER CORONARY SINUS MITRAL VALVE ANNULOPLASTY PROCEDURE AND CORONARY ARTERY AND MYOCARDIAL PROTECTION DEVICE

(75) Inventors: June-Hong Kim, Busan (KR); Robert J. Lederman, Chevy Chase, MD (US); Ozgur Kocaturk, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 436 days.

(21) Appl. No.: 13/468,761

(22) Filed: May 10, 2012

(65) Prior Publication Data

US 2012/0232574 A1  Sep. 13, 2012

Related U.S. Application Data

(62) Division of application No. 12/514,990, filed as application No. PCT/US2007/023876 on Nov. 13, 2007, now Pat. No. 8,211,171.

(60) Provisional application No. 60/858,716, filed on Nov. 14, 2006, provisional application No. 60/932,611, filed on May 31, 2007.

(51) Int. Cl.
*A61F 2/24* (2006.01)
*A61F 2/06* (2013.01)
*A61M 25/00* (2006.01)

(52) U.S. Cl.
CPC ............... *A61F 2/2451* (2013.01); *A61F 2/06* (2013.01); *A61F 2002/068* (2013.01); *A61F 2210/0014* (2013.01); *A61F 2220/0075* (2013.01); *A61F 2230/0045* (2013.01); *A61F 2250/0037* (2013.01); *A61F 2250/0065* (2013.01);

(Continued)

(58) Field of Classification Search
CPC ..................... A61M 25/0021; A61M 25/0041; A61M 25/0052; A61M 25/0152; A61M 25/0029; A61M 2025/006; A61M 2025/0059; A61M 27/008; A61F 2002/068; A61F 2/2451
See application file for complete search history.

(56) References Cited

U.S. PATENT DOCUMENTS

| | | |
|---|---|---|
| 4,917,698 A | 4/1990 | Carpentier et al. |
| 5,041,130 A | 8/1991 | Cosgrove et al. |

(Continued)

FOREIGN PATENT DOCUMENTS

| | | |
|---|---|---|
| EP | 1 022 022 | 11/1999 |
| WO | WO 95/06447 | 3/1995 |

(Continued)

OTHER PUBLICATIONS

Alfieri, et al., "Future of transcatheter repair of the mitral valve", Abstract Only, *American Journal of Cardiology*, vol. 96, No. 12A, pp. 71L-75L, 2005.

(Continued)

*Primary Examiner* — Thomas J Sweet
*Assistant Examiner* — Cheryl Miller
(74) *Attorney, Agent, or Firm* — Klarquist Sparkman, LLP

(57) ABSTRACT

A protective device or bridge comprising a central arch is suitable to be placed between an annuplasty device placed in the coronary sinus and an underlying coronary artery to inhibit transmission of compressive force on the coronary artery by the annuplasty device.

21 Claims, 11 Drawing Sheets

(52) U.S. Cl.
CPC .... *A61M25/0041* (2013.01); *A61M 2025/0042* (2013.01); *A61M 2025/0059* (2013.01)

(56) References Cited

U.S. PATENT DOCUMENTS

| | | | |
|---|---|---|---|
| 5,061,277 | A | 10/1991 | Carpentier et al. |
| 5,064,431 | A | 11/1991 | Gilbertson et al. |
| 5,104,407 | A | 4/1992 | Lam et al. |
| 5,201,880 | A | 4/1993 | Wright et al. |
| 5,290,300 | A | 3/1994 | Cosgrove et al. |
| 5,350,420 | A | 9/1994 | Cosgrove et al. |
| 5,476,528 | A | 12/1995 | Trimm et al. |
| 5,972,030 | A | 10/1999 | Garrison et al. |
| 6,402,781 | B1 | 6/2002 | Langberg et al. |
| 6,485,760 | B2 | 11/2002 | Matsuyama |
| 6,716,459 | B2 | 4/2004 | Matsuyama |
| 6,726,716 | B2 | 4/2004 | Marquez |
| 7,073,511 | B2 * | 7/2006 | Schroeppel ............... A61F 2/04 128/898 |
| 7,090,695 | B2 | 8/2006 | Solem et al. |
| 2002/0128701 | A1 * | 9/2002 | Winters ........................ 623/1.11 |
| 2002/0198591 | A1 * | 12/2002 | Stergiopulos ............. A61F 2/01 623/1.15 |
| 2003/0078465 | A1 | 4/2003 | Pai et al. |
| 2003/0083538 | A1 | 5/2003 | Adams et al. |
| 2003/0130731 | A1 * | 7/2003 | Vidlund ........... A61B 17/00234 623/2.37 |
| 2004/0098116 | A1 | 5/2004 | Callas et al. |
| 2004/0102840 | A1 | 5/2004 | Solem et al. |
| 2004/0220657 | A1 | 11/2004 | Nieminen et al. |
| 2004/0254600 | A1 | 12/2004 | Zarbatany et al. |
| 2005/0027351 | A1 | 2/2005 | Reuter et al. |
| 2005/0027353 | A1 * | 2/2005 | Alferness et al. ............. 623/2.11 |
| 2005/0038506 | A1 | 2/2005 | Webler et al. |
| 2005/0137451 | A1 | 6/2005 | Gordon et al. |
| 2005/0216039 | A1 | 9/2005 | Lederman |
| 2005/0222488 | A1 * | 10/2005 | Chang ............. A61B 17/00234 600/37 |
| 2006/0106279 | A1 | 5/2006 | Machold et al. |
| 2006/0184242 | A1 | 8/2006 | Lichtenstein |
| 2007/0027392 | A1 | 2/2007 | Schwartz |
| 2007/0073391 | A1 | 3/2007 | Bourang et al. |
| 2007/0123978 | A1 * | 5/2007 | Cox ............................... 623/2.1 |
| 2010/0114299 | A1 * | 5/2010 | Ben Muvhar ............. A61F 2/91 623/1.24 |
| 2011/0054597 | A1 | 3/2011 | Kim |
| 2015/0157459 | A1 * | 6/2015 | Macoviak ............. A61F 2/2445 623/2.11 |

FOREIGN PATENT DOCUMENTS

| | | |
|---|---|---|
| WO | WO 01/54618 | 8/2001 |
| WO | WO 02/100240 | 12/2002 |
| WO | WO 03/037171 | 5/2003 |
| WO | WO 2004/045378 | 6/2004 |
| WO | WO 2006/116129 | 11/2006 |
| WO | WO 2006/132880 | 12/2006 |

OTHER PUBLICATIONS

Block, "Percutaneous transcatheter repair for mitral regurgitation", Abstract Only, *Journal of Interv. Cardiology*, vol. 6, pp. 547-551, 2006.

Chinzei, et al., "MR Compatibility of Mechatronic Devices: Design Criteria", *Int. Conf Med. Image Comput. Assist Interv.*, vol. 2, pp. 1020-1031, 1999.

De Silva, et al., "X-Ray Fused With Magnetic Resonance Imaging (XFM) to Target Endomyocardial Injections", *Circulation*, vol. 114, pp. 2342-2350, 2006.

Dieter, "Percutaneous valve repair: Update on mitral regurgitation and endovascular approaches to the mitral valve", *Applications in Imaging—Cardiac Interventions*, pp. 11-14, 2003.

Feldman, et al., "Percutaneous treatment of valvular heart disease: catheter-based aortic valve replacement and mitral valve repair therapies", Abstract Only, *American Journal of Geriatric Cardiology*, vol. 15, No. 5, pp. 291-301, 2006.

Mack, "New Techniques for percutaneous repair of the mitral valve", *Heart Fail. Rev.*, vol. 11, pp. 259-268, 2006.

Maniu, et al., "Acute and chronic reduction of functional mitral regurgitation in experimental heart failure by percutaneous mitral annuloplasty", Abstract Only, *Journal of American Coll. Cardiol.*, vol. 44, No. 8, pp. 1652-1661, 2004.

Maselli, et al., "Percutaneous Mitral Annuloplasty: An Anatomic Study of Human Coronary Sinus and Its Relation With Mitral Valve Annulus and Coronary Arteries", *Circulation*, vol. 114, pp. 377-380, 2006.

Webb, et al., "Percutaneous Transvenous Mitral Annuloplasty: Initial Human Experience With Device Implantation in the Coronary Sinus", *Circulation*, vol. 113, pp. 851-855, 2006.

* cited by examiner

TRANSCATHETER CORONARY SINUS MITRAL VALVE ANNULOPLASTY PROCEDURE AND CORONARY ARTERY AND MYOCARDIAL PROTECTION DEVICE

CROSS-REFERENCE TO RELATED APPLICATIONS

This application is a divisional of U.S. patent application Ser. No. 12/514,990, filed May 14, 2009, now U.S. Pat. No. 8,211,171, which is the U.S. National Stage application of PCT/US2007/023876, filed Nov. 13, 2007, which in turn claims the benefit of U.S. Provisional Application No. 60/858,716 filed Nov. 14, 2006 and U.S. Provisional Application No. 60/932,611 filed May 31, 2007, all of which are incorporated herein in their entirety.

FIELD OF THE DISCLOSURE

The present disclosure relates to annuloplasty techniques and devices in which tensioning elements are placed in the coronary sinus to perform mitral valve annuloplasty and treat mitral valve regurgitation.

BACKGROUND

Mitral valve regurgitation is a common cardiac valve disorder that can be caused by a primary valvular problem (such as damaged valve leaflets) or functional problems that impair leaflet coaption. A common cause of functional mitral valve regurgitation is dilated cardiomyopathy caused by myocardial infarction, chronic myocardial ischemia, hypertension, myocarditis, or other causes of heart muscle injury. Enlargement of the mitral annulus and left ventricular cavity produce mitral valvular insufficiency that can cause volume overload that further exacerbates the underlying myopathy and worsens the valvular insufficiency. Mitral valve repair can reduce mitral regurgitation and correct secondary mitral annular dilation to thereby improve mitral valve leaflet coaption. One such repair technique is an annuloplasty procedure, in which the annulus of the valve is surgically reconstructed or augmented by placement of a ring around the valve annulus to reduce its circumferential and septal-lateral dimensions. In patients with congestive heart failure and secondary mitral regurgitation, annuloplasty can provide a long-term symptomatic and survival benefit Traditional mitral valve annuloplasty requires open heart surgery with a sternotomy or thoracotomy and cardiac arrest and cardio-pulmonary bypass. For example, the annuloplasty procedure is performed through a surgical incision in which the effective size of the valve annulus is reduced by attaching a prosthetic annuloplasty ring to the left atrial aspect of the mitral valve annulus. A variety of rigid and flexible annuloplasty rings have been developed for this purpose, such as those shown in U.S. Pat. Nos. 4,917,698; 5,041,130; 5,061,277; 5,064,431; 5,104,407; 5,201,880; and 5,350,420. Although very effective, this open-heart procedure is accompanied by substantial morbidity and prolonged convalescence. As a result, the procedure often is not offered to patients who are insufficiently symptomatic to justify the surgical risk and morbidity, or to patients who suffer advanced disease, or to patients with substantial co-morbidity.

Percutaneous approaches to mitral valve repair have been developed to reduce the clinical disadvantages of the open-heart procedures. In some percutaneous technique, a prosthesis is advanced in a catheter through the subject's vasculature to the vicinity of the mitral valve. These percutaneous techniques are attractive alternatives to conventional surgical treatment because they do not require open heart surgery or extracorporeal circulation, and can be used in a closed and beating heart. The treatment is potentially less morbid and can be applied to a wider range of patients including those with less severe valvular dysfunction.

Examples of percutaneous mitral valve repair procedures include coronary-sinus shortening devices, transcameral fixtures, endoventricular annular plication, and direct leaflet stapling. Coronary sinus annuloplasty techniques have been disclosed, for example, in U.S. Pat. Nos. 6,402,781 and 7,090,695 as well as U.S. Patent Publication Nos. 2004/0254600; 2005/0027351; and 2007/0073391. Some trans-sinus approaches aim to improve mitral valve coaptation by introducing a prosthesis into the coronary sinus to exert forces that reduce the circumference of the posterior mitral annulus or move the posterior annulus toward the anterior leaflet. Coronary sinus methods take advantage of the proximity of the coronary sinus to the mitral valve annulus, such that the pressure of the prosthesis in the coronary sinus pushes the fibrous annulus or the nearby atrial wall inward to reduce the diameter of the annulus.

However, these techniques have shown only limited success in establishing circumferential tension that characterizes effective surgical ring annuloplasty. The sinus-shortening devices have induced only local shortening across the mitral commissures but do not adequately reduce the septal-lateral separation that characterizes functional mitral valve regurgitation. The leaflet procedures have not been able to reduce annular dilation and they can also impair the normal dynamic line of mitral valve coaption that accommodates a range of volumes and inotropic states.

A more recent improvement of percutaneous annuloplasty is coronary sinus transcatheter-mitral-valve cerclage annuloplasty in which a tensioning material is placed around the mitral valve annulus using a catheter, such as a steerable guide wire or canalization catheter. Certain cerclage trajectories can compensate for coronary sinus anatomy that is remote from the mitral valve annulus, by rotating the plane of circumferential tension toward the left ventricular outflow tract. In cerclage, a continuous strand of tensioning material (such as suture material) is applied along a pathway that extends at least partially through the coronary sinus and then reenters the right side of the heart, for example by passing through a basal septal perforator vein and penetrating a small distance through septal myocardium. The tensioning material is placed with the assistance of imaging technologies that may include X-ray fluoroscopy, magnetic resonance imaging, intracavitary or external ultrasound, electroanatomic mapping, X-ray computed tomography or a combination (fusion) of any of these imaging technologies.

SUMMARY OF THE DISCLOSURE

Trans-sinus approaches that use the cerclage technique or other indwelling coronary sinus prostheses can have limiting drawbacks, however, because the coronary sinus and its branches have now been found to cross the outer diameter of major coronary arteries in a majority of humans. As a result, pressure applied by any prosthetic device in the coronary sinus (such as tension on the annuloplasty device) can compress the underlying coronary artery and induce myocardial ischemia or infarction. In particular, the coronary sinus usually extends superficial to the circumflex coronary artery and its marginal branches near the great cardiac vein, and trans-sinus annuloplasty transmits pressure sufficient to constrict or occlude the underlying coronary artery. Whether coronary obstruction occurs during coronary sinus annuloplasty depends on the spatial relationship between the coronary artery and vein. In a majority of humans, the coronary vein crosses over the left circumflex artery, which has limited the usefulness of coronary sinus annuloplasty. Given the foregoing, there is a need for methods that avoid constricting coronary artery branches during trans-sinus annuloplasty.

Devices and methods are described herein for protecting underlying myocardial structures such as myocardial tissue or coronary artery branches from constriction during trans-sinus mitral annuloplasty. The device can protect a coronary vessel from compression during mitral annuloplasty in which an annuloplasty element, such as a tensioning device, extends at least partially through the coronary sinus over a coronary artery. The device is a surgically sterile bridge configured for placement within the coronary sinus at a location where the coronary sinus passes over a coronary artery, so that the protection device provides a support for a mitral annuloplasty element, such as a compressive prosthesis, including a tension element when it is placed under tension. The protection device has an arch of sufficient rigidity and dimensions to support the tensioning element over the coronary artery, redistribute tension away from an underlying coronary artery, and inhibit application of pressure to the underlying artery, for example when an annuloplasty tension element is placed under tension during mitral annuloplasty.

In particular embodiments, the protective device is a support interposed in the coronary sinus between the annuloplasty device and the coronary artery. In one disclosed example, the protective device has guides on it that retain the annuloplasty device on the support. Such a guide can take the form of an internal lumen that extends the length of the support and through which a mitral annuloplasty tension element can extend so that the protective device supports the tension element away from the coronary artery. The device may be substantially tubular so that the tensioning element is contained within the protective device and supported in spaced relationship to the coronary artery. The arch may be configured to extend between a proximal end and a distal end that are substantially collinear with one another so that the ends form stabilizing members such as feet that retain the bridge in position over the coronary artery.

In particularly advantageous examples, the central arch bridges a linear distance at its base of from about 0.5 inches to about 0.6 inches, for example about 0.52 inches to about 0.55 inches, such as about 0.536 inches. In disclosed examples the central arch is from about 0.15 inches to about 0.16 inches high, for example about 0.1545 inches high, and the bridge has an outer diameter that is from about 0.04 to about 0.05 inches (for example 0.045 inches) along its entire length, and an inner diameter that is from about 0.025 inches to about 0.035 inches (for example 0.030 inches) along its entire length. In other examples, the protective device is made of a shape memory material, such as nitinol.

The device may be used in methods of improving the function of a mitral valve in a subject in which an annuloplasty element, for example an element that exerts compressive remodeling forces on the mitral valve (such as a tensioning element), is introduced at least partially around the mitral valve, for example at least partially through the coronary sinus and over a coronary artery. The protective device is placed between the annuloplasty element and the coronary artery, with the annuloplasty element separated from the underlying coronary artery by the bridge of the device. Compressive remodeling forces are exerted by the annuloplasty device (for example by applying tension on a tensioning element to alter the shape or configuration of the mitral valve annulus to reduce its circumference) while supporting the annuloplasty element on the bridge to inhibit application of pressure to the coronary artery. The function of the mitral valve in the patient is thereby improved without impairing coronary blood flow.

In some embodiments, the annuloplasty element is introduced at least partially around the mitral valve by advancing the annuloplasty element in an endovascular catheter through the vascular system of the subject to the heart, and introducing the annuloplasty element and the protective device from the catheter into the coronary sinus through a coronary sinus ostium. The annuloplasty element may, for example be a tensioning element such as a ligature, which in some embodiments is suture material. In those embodiments in which the protective device includes an internal lumen, the annuloplasty element extends through the lumen of the protective device over the coronary artery so that the annuloplasty element is supported by the protective device. The protective device can be integrated directly into the annuloplasty element, such as a resilient or expandable device, or a tensioning element or tensioning material.

In other embodiments, this disclosure provides a method of improving function of a mitral valve in a subject who has mitral regurgitation by performing a mitral valve cerclage annuloplasty. In a particular disclosed example of the procedure, a guiding catheter is percutaneously inserted through the vasculature of a subject. The guiding catheter is introduced through the coronary sinus and over an underlying coronary artery or other heart structure that is to be protected with the device. In one example, the catheter is introduced into the great cardiac vein, and a steerable microcatheter or other coaxial guiding catheter or steering device introduces a guidewire or other penetrating device (such as a needle, radiofrequency energy ablation device or laser ablation device) into a basal blood vessel such as the first septal coronary vein. From there the penetrating device directly traverses under imaging guidance the septal myocardium or annulus fibrosis and reenters the right ventricle or right atrium.

The guidewire is then retrieved using, for example, a vascular snare, and the guiding catheter and guidewire are replaced with a tensioning system. The protective device is then introduced through the guiding catheter over or in tandem with the tensioning system so as to protect an underlying coronary artery when tension is introduced to perform the annuloplasty. The location of the jeopardized coronary artery is identified, for example, by radiocontrast angiography or by fusion of prior computed tomography angiography and live X-ray or using intravascular ultrasound. In an alternative approach, coronary veins are entered in the other direction from the right atrium or right ventricle under imaging guidance into a branch of the coronary sinus.

Tension is applied through, for example, suture material exchanged for the cerclage guidewire. Tension can be applied through both ends of the suture as they are externalized at the point of vascular access. Tension is applied under imaging guidance until the desired degree of mitral annular circumferential reduction is accomplished, or until the mitral valve regurgitation is reduced, or until other deleterious endpoints are achieved such as mitral valve inflow obstruction. Tension is secured using a tension fixation device applied to both ends of the suture at the right atrium or right ventricle where the two cerclage trajectories cross, or at the point of vascular access, or in between the two. Tension is delivered by counterpressure against the fixation device, for example, applied through a delivery catheter. Before fixation, tension can be released or reduced, for example, to reposition the protection device or to achieve a lower degree of mitral annular circumferential reduction.

In some embodiments, the protection device can be incorporated during manufacture into the tension suture device, such that longitudinal displacement of the tension suture material alters the circumferential position of the protection device in relation to the underlying coronary arteries. This embodiment allows the protection device to be positioned over the protected coronary artery by longitudinal displacement of the tension suture material.

The protection device can be incorporated, by modification, into a coronary sinus shortening system already publicly disclosed, tested, or marketed, for the treatment of mitral valve regurgitation.

In another described embodiment of a transcatheter coronary sinus procedure, annuloplasty is performed by advancing a wire through the catheter into the coronary sinus to a coronary vein branch such as an anterolateral cardiac vein, and then across myocardial or fibrous tissue of the heart through the left ventricular chamber, and further across myocardium into the right ventricular or right atrial cavity. The wire is then exchanged to introduce tensioning material through the coronary sinus, and tension is applied on the tensioning material to alter the shape of the heart or valves and reduce unwanted, for example deleterious, cardiac remodeling or valvular regurgitation.

Different lengths of protection devices may be made available to offer protection for narrow or wide segments of single or multiple coronary arteries potentially compressed by the cerclage or other annuloplasty device. Similarly, multiple protection devices may be used in tandem to offer protection to adjacent or nonadjacent circumferential segments potentially compressed by the cerclage or other annuloplasty device. Similarly the protection devices can be employed to protect other cardiac structures that may be compromised by the annuloplasty tension element, such as from focal erosion of the myocardium or laceration of the tricuspid valve leaflet.

BRIEF DESCRIPTION OF THE FIGURES

FIG. 1 shows two embodiments of the protective device.

FIG. 3 is a set of drawings showing the region of the heart involved in trans-sinus coronary annuloplasty and illustrating the use of the protective device to prevent pinching of the coronary artery when tension is applied to a cerclage tensioning device.

DETAILED DESCRIPTION OF SEVERAL EMBODIMENTS

I. Explanation of Terms

Figure 1A:
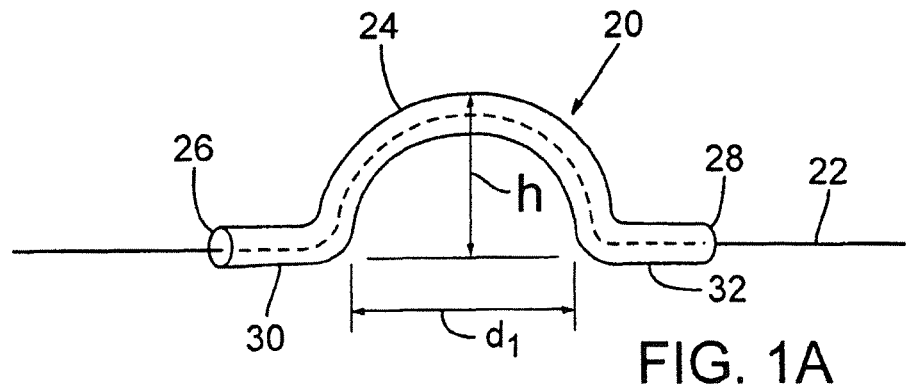
FIG. 1A is a side elevational view of a first embodiment of the protective device which has a central curved arch and two substantially linear ends that extend in the same plane as one another and function as support feet. The protective device has a hollow lumen through which a ligature (for example, and without limitation, a wire or suture) can pass, as shown by the broken line.

Unless otherwise noted, technical terms are used according to conventional usage. In order to facilitate review of the various embodiments of the disclosure, the following explanation of terms is provided:

"Annuloplasty element" refers to a device that induces reshaping of an annulus of the heart to repair valvular insufficiency. Such devices include those that are placed in the coronary sinus and exert their action by compressive forces on the annulus, for example by expansion of a resilient annuloplasty element, or placement of the annuloplasty element under tension, as in cerclage annuloplasty.

The term "comprises" means "includes without limitation." Thus, "comprising a guiding catheter and a guide wire" means "including a guiding catheter and a guide wire," without excluding additional elements.

The term "guide wire" refers to a simple guide wire, a stiffened guide wire, or a steerable guide-wire catheter that is capable of puncturing and/or penetrating tissue. The guidewire also can deliver energy to augment its ability to penetrate tissue, for example by puncturing it, delivering radiofrequency ablative energy or by delivering laser ablative energy. These are examples of a "penetrating device," which is a device capable of penetrating heart tissue, such as the myocardium.

As used herein, the term "ligature" is meant to encompass any suitable tensioning material and is not limited to only suture material. The term "tensioning material" or "ligature" includes sutures and annuloplasty wires.

A "mitral valve cerclage annuloplasty" refers to an annuloplasty procedure in which a tensioning element is placed through at least a portion (and preferably all) of the coronary sinus so that the circumferential tension is delivered around the mitral valve annulus and so that a tensioning element can be placed under selective degrees of tension to perform the annuloplasty. An example of cerclage annuloplasty is disclosed in co-pending prior application Ser. No. 11/127,112 (U.S. Patent Publication No. 2005/0216039), and the disclosure of the description of that technique is incorporated herein by reference. However, the mitral valve cerclage annuloplasty technique also includes other cerclage trajectories, such as those disclosed herein, including a trajectory through a proximal coronary septal perforator vein and myocardium or annulus fibrosis interposing between that vein and the right ventricle or right atrium to create circumferential cerclage annuloplasty tension.

The protective (or protection) device disclosed herein can be made of an "MRI-compatible" material. Such materials are safe to use in the body during magnetic resonance imaging of the body, and do not substantially affect imaging quality of the MRI. An "MRI-safe" material is one that does not add substantial risk to a human or equipment by placing it in the magnetic field of an MR environment. Examples of MRI-compatible materials are non-ferrous materials, such as ceramics, plastics and non-magnetic composite materials. Austenitic stainless steels (of the 300 series) are neither ferromagnetic nor paramagnetic and therefore are MRI-compatible. Titanium and aluminum are MRI-compatible, even though they are not ideally paramagnetic. Particularly disclosed MRI-compatible materials of which the protective device may be made include nitinol, MP35N and cobalt-chromium alloys.

"Tensioning material" is any material suitable to perform a coronary sinus mitral valve cerclage annuloplasty, in which an encircling material is placed under tension to remodel the mitral valve annulus. Examples of suitable tensioning materials are the ligature materials already described.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

Figure 1B:
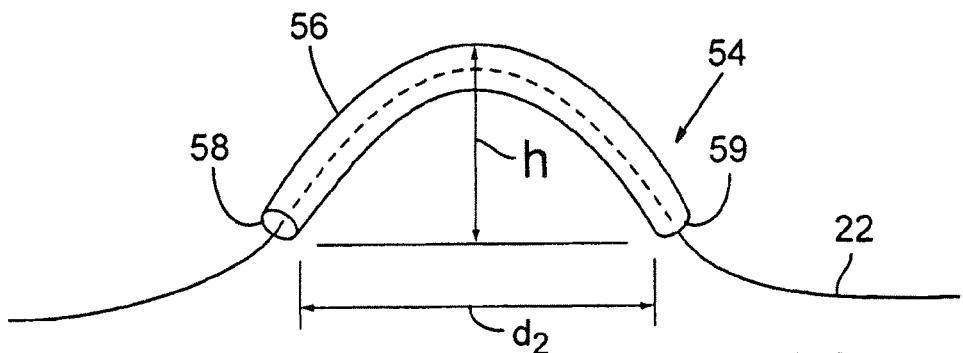
FIG. 1B is a side elevational view of another embodiment of the protective device. In this embodiment, the protective device has a central curved portion and no support feet.

II. Protection Device to Protect Coronary Arteries During Mitral Valve Cerclage Annuloplasty (FIGS. 1A, 1B and 1C)

Coronary sinus mitral valve cerclage annuloplasty is an example of a percutaneous mitral valve repair procedure for which the disclosed protective device can be used. Although the device and methods of its use are broadly applicable to any prosthetic annuloplasty element placed in the coronary sinus, the methods will be described in connection with the particular example of cerclage annuloplasty. This specific example should not be construed to limit the procedure to use with cerclage annuloplasty, but only to illustrate its use in a particular embodiment.

Cerclage annuloplasty percutaneous repair carries a lower risk or morbidity than conventional mitral valve surgery, and thus can be used in patients who have less severe or more severe valvular dysfunction. Placing cerclage ligatures at least partially through the coronary sinus takes advantage of the proximity of the coronary sinus to the mitral valve annulus, and of the ready catheter access to the coronary sinus and tributary veins. These approaches also have limiting drawbacks, however, in that compression of nearby coronary artery branches is a serious risk in a majority of human subjects. The coronary sinus usually runs superficial to the circumflex coronary artery and its marginal branches near the great cardiac vein, and therefore trans-sinus annuloplasty can transmit pressure sufficient to constrict or occlude the coronary artery or its branches. Devices and methods that prevent this compression of the coronary artery, such as those disclosed herein, can dramatically increase the safety and efficacy of trans-sinus mitral cerclage annuloplasty.

An exemplary transcatheter-mitral-valve-cerclage annuloplasty involves the introduction of a tensioning material or device around the mitral valve annulus using a guiding catheter and a secondary catheter, such as a steerable microcatheter directing coaxial guide wires or canalization catheter. Access to the area around the mitral-valve annulus can be accomplished using a variety of percutaneous approaches, including access from and through the coronary sinus. In particular embodiments, a continuous strand of tensioning material also referred to as a cerclage ligature (for example, and without limitation, a tensioning material such as a wire or suture) is applied around the mitral-valve annulus along a pathway that, in certain embodiments, includes an extra-anatomic portion. For example (and without limitation), the tensioning material can traverse a region between the anterobasal-most portion of the coronary sinus and the coronary-sinus ostium. As another non-limiting example, tensioning material can be applied across the atrial aspect of the mitral valve from the posterolateral aspect to the anterior aspect of the coronary sinus, or from the septal aspect to the lateral aspect of the mitral-valve annulus. This procedure reduces the mitral annular cross-sectional area and septal-lateral wall separation, thereby restoring a line of coaptation of the mitral valve.

Because it has now been found that mitral annuloplasty via the coronary sinus unintentionally transmits pressure sufficient to constrict or occlude the underlying coronary artery, the devices disclosed herein have been developed to increase the safety and efficacy of the procedure. The disclosed devices protect an underlying vessel from compression during mitral annuloplasty in which a cerclage ligature extends at least partially through the coronary sinus over a coronary artery. In one embodiment shown in FIG. 1A, the device is a surgically sterile protection device or bridge 20 of a suitable shape and size to permit its introduction through a transvascular catheter into the coronary sinus. The protection device has an internal lumen extending its length through which a mitral cerclage tension element 22 can extend and be placed under tension, and the protection device also includes a central arch 24 of sufficient rigidity and dimensions to inhibit application of pressure to the underlying left circumflex artery when the cerclage tension element is placed under tension during mitral valve annuloplasty. For example, the protection device has a semi-circular shape of sufficient radius to extend closely over an underlying coronary artery to inhibit the transmission of compressive forces from the tension element to the underlying artery. The compressive forces are instead distributed on and along the protection device to protect the artery from compression that impairs myocardial perfusion.

In the embodiment of FIG. 1A, the central arch of the device extends between a proximal end 26 and a distal end 28 of the protection device, and the proximal and distal ends are not curved but extend in substantially the same plane as one another, radially away from the arch, to form stabilizing feet 30, 32 that can rest against a wall of the coronary sinus while straddling a coronary artery to retain protection device 20 in position over the left circumflex artery and bear and distribute the compressive forces that are applied by ligature 22 under tension. The example of the device illustrated in FIG. 1A has a central arch bridging a linear distance d1 at its base of from about 0.5 inches to about 0.6 inches, for instance, from about 0.52 inches to about 0.55 inches, or about 0.536 inches. The illustrated central arch has a height h from about 0.15 inches to about 0.16 inches high, for instance, about 0.1545 inches high. These dimensions are examples of dimensions that can be assumed by the device, which help it conform closely to without occluding a coronary artery.

The illustrated embodiment of the protection device in FIG. 1A is a generally tubular member having an outer diameter from about 0.04 to about 0.05 inches, and the inner diameter is from about 0.025 inches to about 0.035 inches along its entire length. In particular examples, the protection device outer diameter is about 0.045 inches along its entire length, and in other particular examples, the diameter of the inner lumen is from about 0.025 inches to about 0.035 inches along its entire length, for instance, about 0.030 inches along its entire length. In even more particular examples, the central arch bridges a linear distance at its base about 0.536 inches, the central arch is about 0.1545 inches high, the protection device outer diameter is about 0.045 inches, and the inner diameter is about 0.030 inches. In certain examples, the device is made from a shape memory material, for instance a nickel titanium alloy such as nitinol, that allows the device to be deformed (for example toward a linear configuration) that is adaptable to introduction through the vascular system. However, the shape memory material returns to the arched configuration shown in the drawings after the device is deployed from a delivery catheter.

Figure 2:
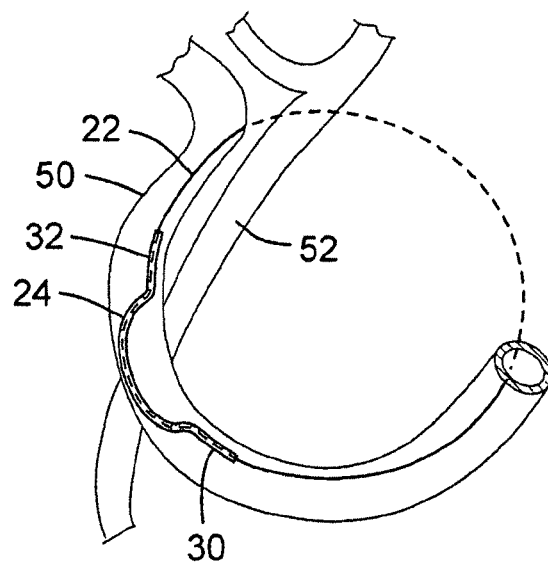
FIG. 2 is a schematic view showing the protective device in position during a cerclage annuloplasty procedure. The ligature encircles the mitral annulus via the coronary sinus, and the protective device is positioned over a coronary artery where the coronary sinus lies superficial to the artery.

FIG. 2 schematically illustrates the use of protection device 20 in a mitral valve cerclage annuloplasty procedure. FIG. 2 depicts tensioning element 22 (suture material) extending through a portion of the coronary sinus 50 over a circumflex coronary artery 52. FIG. 2 shows protection device 22 is positioned within coronary sinus 50 with arch 24 extending over coronary artery 52, and feet 30, 32 on either side of coronary artery 52. As tension is placed on tensioning element 22 the support feet 30, 32 are held in place on either side of coronary artery 52 and transmit compressive forces to the wall of coronary sinus 50 instead of on to underlying coronary artery 52.

Figure 3A:
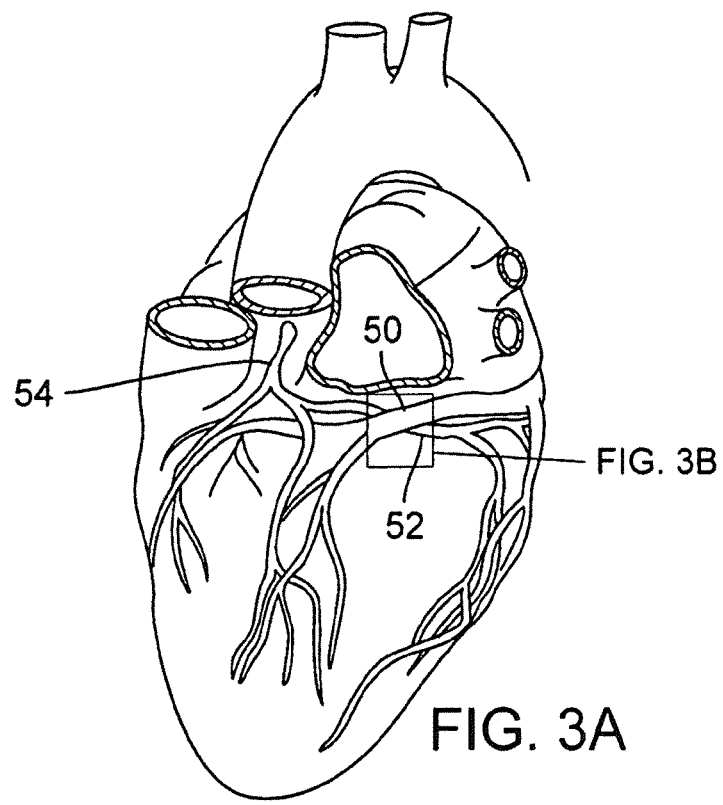
FIG. 3A is a left lateral external perspective view of the heart showing the lateral coronary artery branching from the ascending aorta, the branch of the lateral circumflex artery, and the great cardiac vein.
Figure 3B:
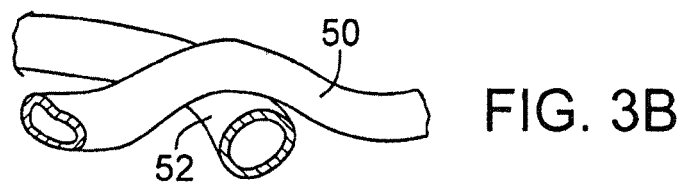
FIG. 3B is an enlarged view of a section of the arteries showing the coronary sinus crossing superficial to the left circumflex coronary artery at the level of the great cardiac vein.
Figure 3C:
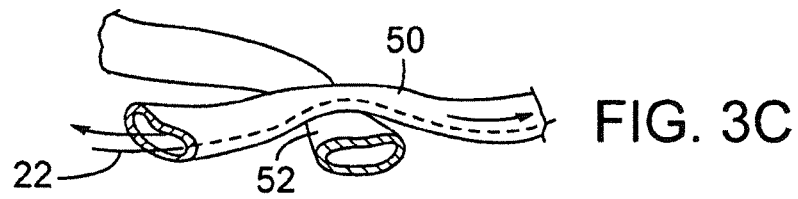
FIG. 3C is a view similar to FIG. 3B but showing placement of a ligature (for example, and without limitation, a wire or suture) during annuloplasty without the protective device in place. When the ligature is tightened during the annuloplasty procedure, pressure is exerted on the branch of the coronary artery, restricting blood flow and myocardial perfusion.
Figure 3D:
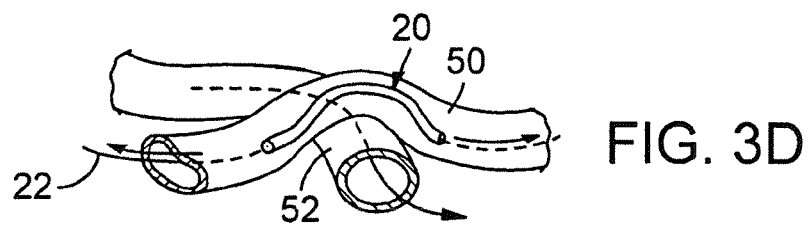
FIG. 3D is an enlarged view of this same structure showing placement of the protective device over the ligature within the coronary sinus and superficial to the coronary artery.

FIGS. 3A, 3B, 3C and 3D provide an alternative view of the function of cerclage annuloplasty protection device 20. FIG. 3A shows the external anatomy of the heart, with coronary sinus 50 extending over a circumflex branch 52 of a left coronary artery 54. FIG. 3B shows an enlarged view of the overlapping relationship of coronary sinus 50 to coronary artery 52. FIG. 3C illustrates tension element 22 placed under tension during cerclage annuloplasty which is compressing underlying coronary artery 52 and interfering with myocardial perfusion. FIG. 3D shows tensioning material 22 extending through protection device 20 which is inhibiting the application of compressive force to coronary artery 52 which therefore remains patent and able to normally perfuse myocardial tissue.

An alternative embodiment of the protection device is shown in FIG. 1B, in which a protection device 54 is tubular so that an internal lumen extends through it to accommodate tension material 22. However this embodiment is shaped into a generally arcuate (for example parabolic or catenary shape instead of semi-circular) arch 56. The distance d2 spanned by arch 58 is slightly greater than the distance d1 spanned by arch 24 in the embodiment of FIG. 3A because of the more gradual slope of arch 44. Protection device 54 of FIG. 3 also does not have the support feet of the embodiment shown in FIG. 3A, and compressive forces are distributed directly from proximal and distal ends 58, 59 of protection device 50 to a wall of the coronary sinus at a position other than over an underlying coronary artery.

The protection device can assume a variety of shapes and configurations that support the tensioning material away from an underlying coronary artery. The protection device can be pre-shaped to the desired configuration, or it can be made of a memory alloy material that is generally linear when being advanced through the guidance catheter but assumes the desired protection device shape once it is deployed from the guidance catheter over the tensioning material.

Although the illustrated protection devices are tubular, a tubular structure is not necessary. For example, the protective device can take the form of a support or bridge having an open top on which the tensioning material is supported. The support would preferably have side guides (such as curved or upright members) that help retain the tensioning material on the support by resisting lateral forces that could dislodge the tensioning material from the support, while permitting longitudinal movement of the tensioning material along the support.

III. Percutaneous Mitral Valve Cerclage Annuloplasty

A. Mitral Regurgitation

Regurgitation (leakage) of the mitral valve or tricuspid valve can result from many different causes, such as ischemic heart disease, myocardial infarction, acquired or inherited cardiomyopathy, congenital defect, traumatic injury, infectious disease, and various forms of heart disease. Primary heart muscle disease can cause valvular regurgitation through dilation, resulting in expansion of the valvular annulus leading to malcoaptation of the valve leaflets through overstretching, degeneration, or rupture of the papillary muscle apparatus, or through dysfunction or malpositioning of the papillary muscles. This regurgitation can cause heart rhythm abnormalities such as atrial fibrillation, which itself can cause inexorable deterioration in heart muscle function. Such deterioration can be associated with functional impairment, congestive heart failure and significant pain, suffering, lessening of the quality of life, or even premature death.

A less dangerous, minimally invasive procedure, such as percutaneous annuloplasty, permits more patients to undergo mechanical treatment of valvular regurgitation.

B. Percutaneous Cerclage Annuloplasty

Because the risks and complications of surgery are reduced (compared with open-heart surgery), catheter-based heart-valve procedures are suitable for a broader population of patients. Disclosed herein are devices and methods for catheter-based valve repair that can be used to repair damaged or malfunctioning cardiac valves, for instance, by re-apposing valve leaflets by percutaneous-cerclage annuloplasty (reconstruction or augmentation of the ring or annulus of a defective cardiac valve). In some instances, percutaneous cerclage annuloplasty is used to deliver circumferential or radial tensioning devices. Examples of some of these procedures are described in detail in WO2004/045378 and US 2005/0216039, which are incorporated herein by reference.

In general, the system used to carry out an annuloplasty procedure can include a guiding catheter (GC), such as a preformed transjugular balloon-tipped guiding catheter which is introduced into the coronary (venous) sinus. A retrograde coronary radiocontrast venogram pressurizes and visualizes the great cardiac vein and septal perforator veins. A high performance guidewire designed for coronary artery recanalization may be steered using a deflectable microcatheter into the great cardiac vein and thereafter into a basal septal perforator vein.

In general, an annuloplasty procedure also can include using an imaging system to image the internal bodily tissues, organs, structures, cavities, and spaces of the subject being treated. For example, transmitter or receiver coils can be used to facilitate active-device navigation using an imaging system, such as magnetic-resonance imaging (MRI). This imaging can be conducted along arbitrary or predetermined planes using various imaging methods based on X-ray technologies, X-ray fluoroscopy, MRI, electromagnetic-positron navigation, video technologies (such as endoscopy, arthroscopy, and the like), ultrasound, and other such technologies. In some embodiments, real-time MRI (rtMRI), intracardiac ultrasound, or electromagnetic guidance is employed. A particularly useful adjunct in cerclage annuloplasty is XFM, in which X-Ray is used with MRI to target myocardial structures, for example to help guide the annuloplasty wire in its trajectory through the structures of the heart. The XFM technique is disclosed, for example, in de Silva et al., *Circulation* 114:2342-2350 (2006).

The guiding catheter enables percutaneous access into a subject's body, for example, percutaneous access to the heart, such as a chamber of the heart through an arm, neck, or leg vein. In some embodiments, the guiding catheter is designed for access to the ventricle and/or atrium of the heart. The guiding catheter permits introduction of one or more secondary catheters, including a valve-manipulation catheter or microcatheter or canalization-needle catheter. The secondary catheter (or catheters) is used to treat, affect, or manipulate an organ, tissue, or structure of interest in the subject's body, such as the heart or particular structures within the heart. If the guiding catheter is used for percutaneous (or other) access to the heart, the guiding catheter permits introduction of one or more secondary catheters, such as a valve-manipulation catheter, into the heart while maintaining hemostasis. The secondary catheters may be coaxial or adjacent to each other, or may be introduced from multiple points of access outside the body.

Guiding catheters are available in different shapes to suit the appropriate component of the mitral-valve-repair procedure. For example, guiding catheter shapes can be provided to suit different coronary sinuses with different radii of curvature, to suit different coronary veins, transaortic as well as transseptal access routes, or to suit atria and ventricles of different calibers. All such shapes can be accommodated with appropriate primary, secondary, and tertiary curves. Examples of catheter configurations suitable to perform percutaneous transvascular mitral valve annuloplasty are know in the art and described in detail in U.S. Patent Publication No. 2005/0216039, which description is incorporated by reference herein.

Although any available approach to the coronary sinus may be used, a venous approach is preferred, for example through the jugular vein. As yet another example, the guiding catheter can be introduced into a vein, such as the femoral or jugular vein, and guided through the inferior or superior vena cava into the right ventricle of the heart.

Figure 4A:
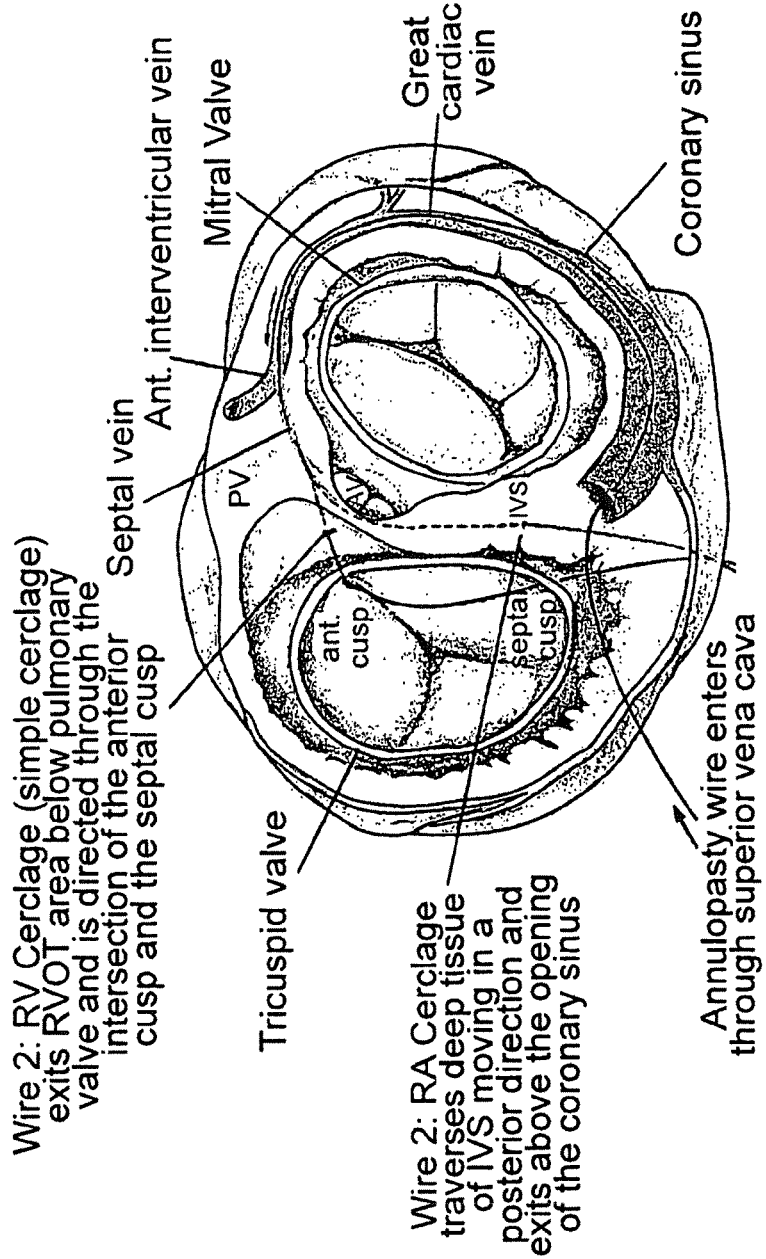
FIG. 4A is a schematic top view of a human heart, taken at the level of the atrioventricular valves, showing in dashed lines two alternative trajectories of the cerclage annuloplasty ligature around the mitral valve.
Figure 4B:
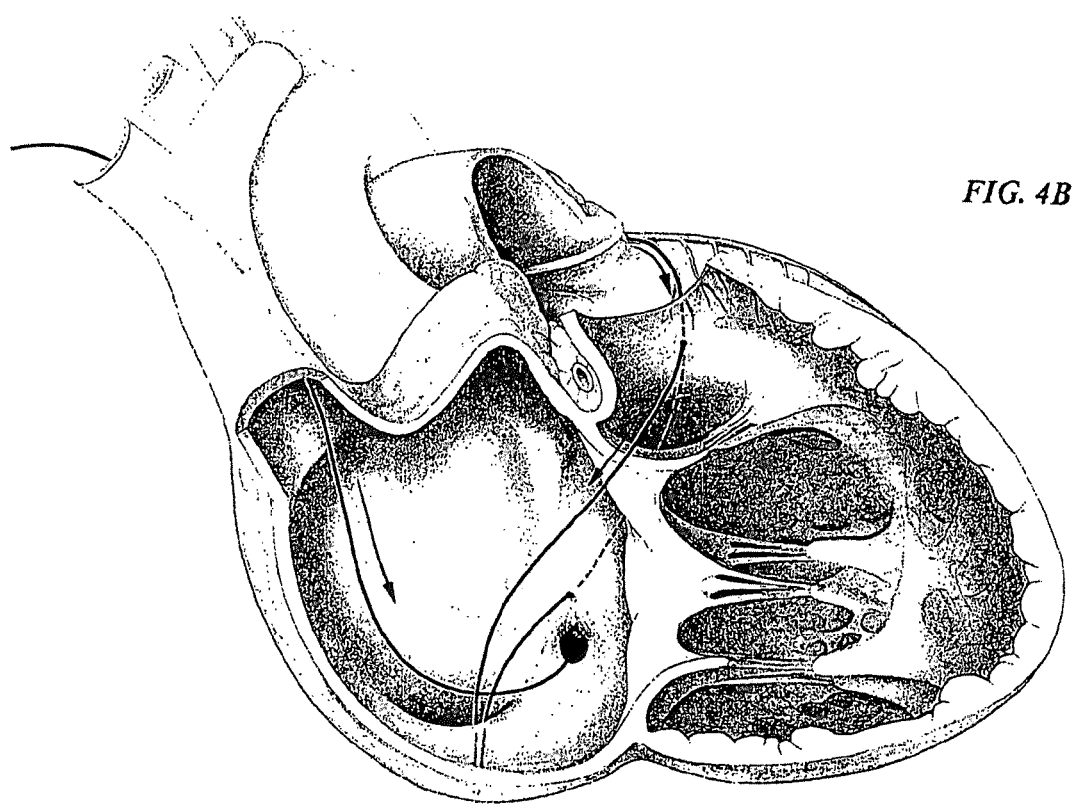
FIG. 4B is a front perspective view of the heart with portions of the myocardial wall broken away to show the cerclage annuloplasty trajectories of FIG. 4B.

Two examples of trajectories for cerclage annuloplasty are shown in FIG. 4A and FIG. 4B. The first trajectory (labeled a "simple" or "RV" trajectory) is one in which the annuloplasty wire enters the right atrium through the superior vena cava and is then introduced through the coronary ostium into the coronary sinus. The wire is advanced through the great cardiac vein into a basal blood vessel, such as a basal septal perforator vein. The wire then exits the septal perforator vein through myocardial interstitium into the right ventricle, re-entering the right atrium along the septal tricuspid valve commisure (at the intersection of the anterior cusp and the septal cusp). The guidewire is then retrieved using, for example, a vascular snare, and the guiding catheter and guidewire are replaced with a different tensioning system, such as a tensioning suture. The replacement can occur, for example, by attaching the tensioning material to the guidewire and advancing the tensioning material along the path of the guidewire as the guidewire is withdrawn. The protection device is then introduced through the guiding catheter over or in tandem with the tensioning system so as to protect an underlying coronary artery when tension is introduced to perform the annuloplasty. The location of the jeopardized coronary artery is identified, for example, by radiocontrast angiography. In an alternative approach, coronary veins are entered in the opposite direction from the right atrium or right ventricle under imaging guidance into a branch of the coronary sinus.

An alternative or "complex" right atrial cerclage trajectory shown in FIGS. 4A and 4B extends further posterior through the basal septal myocardium into the right atrium near the coronary sinus. The wire traverses deep tissue of the septum moving in a posterior direction and exits above the opening of the coronary sinus.

Figure 4C:
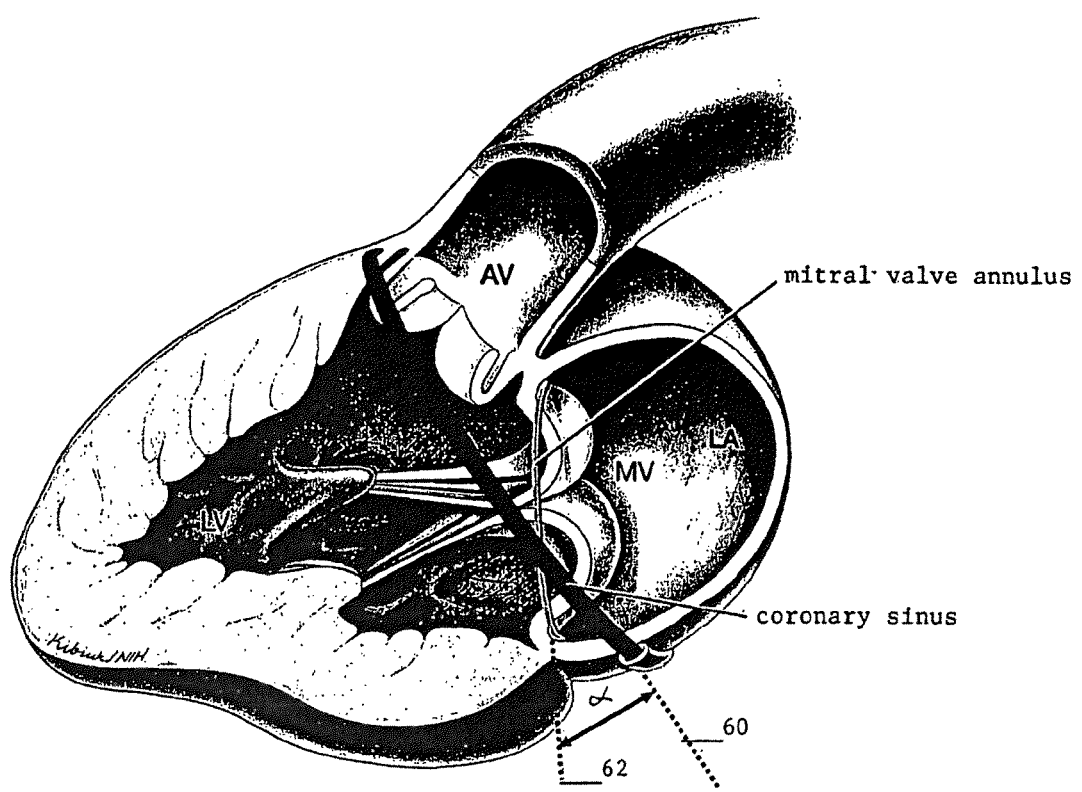
FIG. 4C is a rear perspective view of the heart showing the tilted plane of the coronary sinus cerclage annuloplasty. The drawing schematically illustrates a smaller traditional surgical mitral valve annuloplasty ring over the mitral valve annular plane and the larger coronary artery cerclage in a plane that is tilted to the mitral plane so as to encompass the left ventricular outflow tract.

The plane of the resulting cerclage annuloplasty is shown in FIG. 4C to be related to and in the plane of the coronary sinus 60 such that annuloplasty remains uniquely feasible even if the coronary sinus is remote from the mitral valve annuloplasty. As the figure indicates, the plane of cerclage 60 enhances mitral valve coaptation, even when the coronary sinus is geometrically remote from the mitral valve annulus, because it is "tilted" toward the left ventricular outflow tract. The illustrated angle α between the cerclage plane 60 and the plane of the mitral valve annulus 62 is therefore advantageous. Moreover, the illustrated trajectories of the cerclage annuloplasty induces reciprocal mitral valve coaptation and left ventricular outflow tract relaxation during ventricular systole.

The guide wire is dimensioned to operate with the catheter and is usually longer than the guiding catheter. For example, a guide wire of about 100 to about 250 centimeters in length and about 0.1 to about 2 mm in diameter can be used with the guiding catheter described above. If a secondary catheter, such as a tension delivery catheter, is intended for use with the guiding catheter, that secondary catheter also is dimensioned to operate with the guiding catheter and is usually longer than the guiding catheter.

The guiding catheter can be made of any suitable material or combination of materials that provide both the strength and flexibility suitable to resist collapse by external forces, such as forces imposed during bending or twisting. Exemplary materials include, but are not limited to: polymers, such as polyethylene or polyurethane; carbon fiber; ceramic; or metals, such as nitinol, platinum, titanium, tantalum, tungsten, stainless steel, copper, gold, cobalt-chromium alloy, or nickel. The guiding catheter optionally can be composed of or reinforced with fibers of metal, carbon fiber, glass, fiberglass, a rigid polymer, or other high-strength material. In particular embodiments, the guiding catheter material is compatible with MRI, for example, braided nitinol, platinum, tungsten, gold, or carbon fiber. Additionally, the exterior surfaces of the guiding catheter can be coated with a material or substance, such as Teflon® or other lubricous material that aids with the insertion of the guiding catheter into the body of the subject and/or aids in the movement of the guiding catheter through the subject's body.

Additionally, the guiding catheter can include a deflectable tip, such as a simple deflectable tip having a single degree of axial freedom. Exemplary (non-limiting) fixed-fulcrum and movable-fulcrum-deflectable-tip catheters are commercially available, such as the deflectable-tip catheters described in U.S. Pat. Nos. 5,397,321; 5,487,757; 5,944,689; 5,928,191; 6,074,351; 6,198,974; and 6,346,099. Thus, any suitable fixed-fulcrum or movable-fulcrum deflectable-tip catheter can be adapted for use as a guiding catheter disclosed herein. The guiding catheter also can include structures or mechanisms for aiding in the rotation of the catheter about its longitudinal axis.

The guiding catheter can include a guide collar, handgrip, handle, and other structures or devices at its proximal end that aid in operation of the guiding catheter. Various control mechanisms, including electrical, optical, or mechanical control mechanisms, can be attached to the catheter via a guide collar. For example, a guide wire can be included as a mechanical control mechanism. The guide collar can include additional operational features, such as a grip for aiding manual control of the guiding catheter, markers indicating the orientation of the guiding catheter lumen or subdivided lumens, markers to gauge the depth of guiding catheter advancement, instruments to measure guiding catheter operation or physiological signs of the subject (for example, a temperature gauge or pressure monitor), or an injector control mechanism coupled to the guiding catheter lumen for delivering a small, precise volume of injectate. In some embodiments, the guide collar contains instrumentation electrically coupled to metallic braiding within the guiding catheter, thus allowing the guiding catheter to simultaneously be used as a receiver coil for MRI.

A guide wire used with the system for guiding the guiding catheter into and through a subject's body can be composed of any suitable material, or combination of materials, including the materials described above in relation to the guiding catheter. Exemplary (non-limiting) guide wires are composed of material having the strength and flexibility suitable for use with the device, such as a strand of metal (for example, surgical stainless steel, nitinol, platinum, titanium, tungsten, copper, or nickel), carbon fiber, or a polymer, such as braided nylon. Particular (non-limiting) guide wires are composed of a strand of Nitinol® or other flexible, kink-resistant material.

The guiding catheter or guide wire can include an image-enhancing feature, structure, material, or apparatus, such as a radiopaque marker (for example, a platinum or tantalum band around the circumference of the guide wire) adjacent its distal end. As another example, the guide wire can include etchings or notches, or be coated with a sonoreflective material to enhance images obtained via intravascular, intracardiac, transesophogeal, or other ultrasound-imaging method. As another example, the guide wire can be coated with a T1-shortening or T2*-shortening agent to facilitate passive visualization using MRI. As yet another example, a fiber-optic secondary catheter can be inserted into and through a secondary-catheter lumen of the guiding catheter to assist in visualizing the position of the guide wire within the subject as a guide wire is deployed through the distal guide-wire lumen port.

In some embodiments, the guide wire and/or guiding catheter includes a structure, apparatus, or device at its distal tip useful for penetrating tissue, such as myocardial skeleton, muscle, or connective tissue. For example, the distal tip of the guide wire can be sharpened to a point for puncturing through tissue, or a secondary catheter having a coring mechanism or forceps at its distal tip can be used in conjunction with the guiding catheter. In alternative embodiments, the guide wire can deliver radiofrequency or laser ablative energy to assist with traversal of tissue. However, in alternative embodiments, the distal end of the guide wire is bent to provide a J-shaped or a pigtail-shaped tip to protect against perforation of tissue by the guide wire during manipulation. In still other alternative embodiments, the guide wire itself has a deflectable tip to facilitate traversal of tissue irrespective of natural tissue planes.

One or more secondary catheters can be deployed within the lumen of the guiding catheter. Like the guiding catheter, each secondary catheter has a proximal end and a distal end; however, not all secondary catheters have a lumen. For example, non-lumen secondary catheters can include various probes, such as temperature probes, radiofrequency or cryogenic ablation probes, or solid needles. An exemplary non-limiting secondary catheter is a canalization needle catheter, which can be deployed through the guiding catheter and into a chamber of the heart to place cerclage annuloplasty ligature through the coronary sinus around the mitral valve. A canalization-needle catheter is a type of secondary catheter that can be used to apply a suture to a bodily tissue, organ, or structure of interest.

Ligatures used for the sutures described herein can be composed of any suitable material, such as surgical cotton, cotton tape, linen, or other natural fiber; nylon, polyester, or other polymer; metal, such as surgical stainless steel or nitinol; carbon fiber; or surgical gut. Ligature materials can be used in a woven, braided, or monofilament form. Suitable ligature and suture materials are commercially available from Ethicon, Inc. (Somerville, N.J.) and other companies.

C. Application of Tension

Tension is applied via the annuloplasty cerclage through, for example, suture material exchanged for the cerclage guidewire. Tension can be applied through both ends of the suture as they are externalized at the point of vascular access. Tension is applied under imaging guidance until the desired degree of mitral annular circumferential reduction is accomplished, or until the mitral valve regurgitation is reduced, or until other deleterious endpoints are achieved such as mitral valve inflow obstruction. Tension is secured using a knot or using a tension fixation device applied to both ends of the suture at the right atrium or right ventricle where the two cerclage trajectories cross, or at the point of vascular access, or in between the two. Tension is delivered by counterpressure against the fixation device, for example, applied through a delivery catheter. Before fixation, tension can be released or reduced, for example, to reposition the protection device or to achieve a lower degree of mitral annular circumferential reduction.

As tension is applied, valvular regurgitation is assessed repeatedly and non-invasively by an appropriate imaging technique. Such imaging techniques include X-ray angiography, electromagnetic position detection, MRI, external or intracavitary or intravascular ultrasound, X-ray computed tomography, pressure transducers in an affected chamber such as the left atrium or the pulmonary vein or the pulmonary artery, or a "fusion" or combination of any of the above. After the valvular regurgitation has been reduced (or even eliminated) and a desired tension is achieved, the tension is fixed using a knot delivery system. If the resulting circumferential suture is knotted to form a closed loop, the suture essentially becomes a cerclage suture.

Without further elaboration, it is believed that one skilled in the art can, using this description, utilize the present discoveries to their fullest extent. The following examples are illustrative only, and not limiting of the disclosure in any way whatsoever.

EXAMPLES

Example 1

Figure 5:
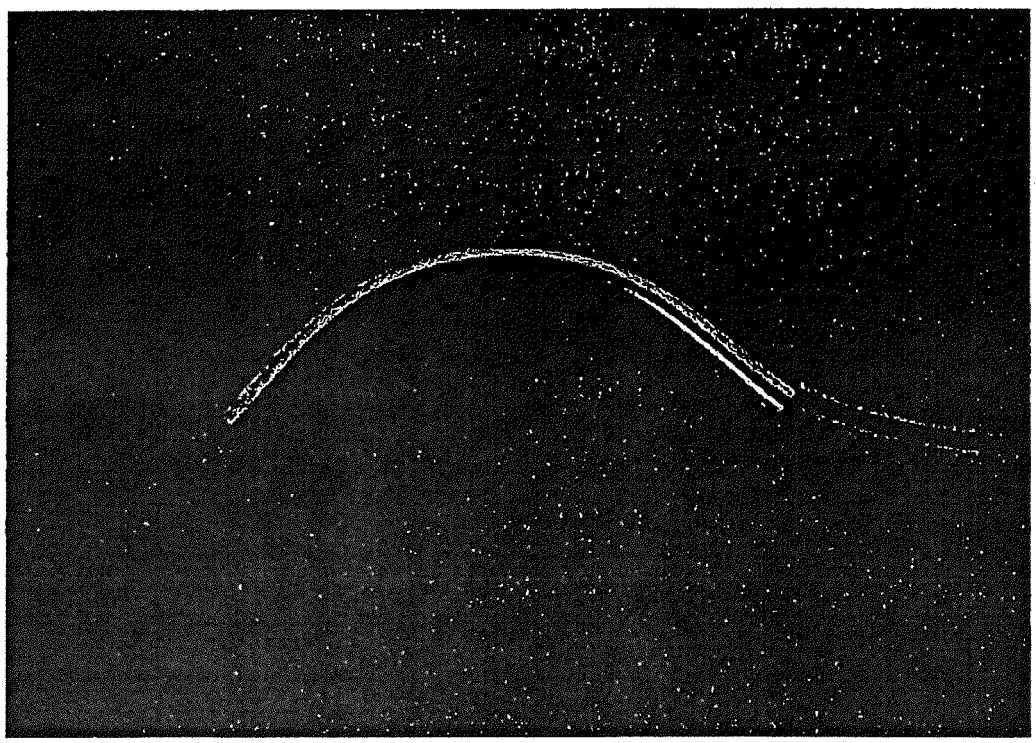
FIG. 5 is a side elevational view of one embodiment of the protective device for protecting a coronary artery from compression during the annuloplasty procedure, showing a device made of nitinol with a surgical suture (black monofilament nylon) ligature extending through the device.
Figure 6:
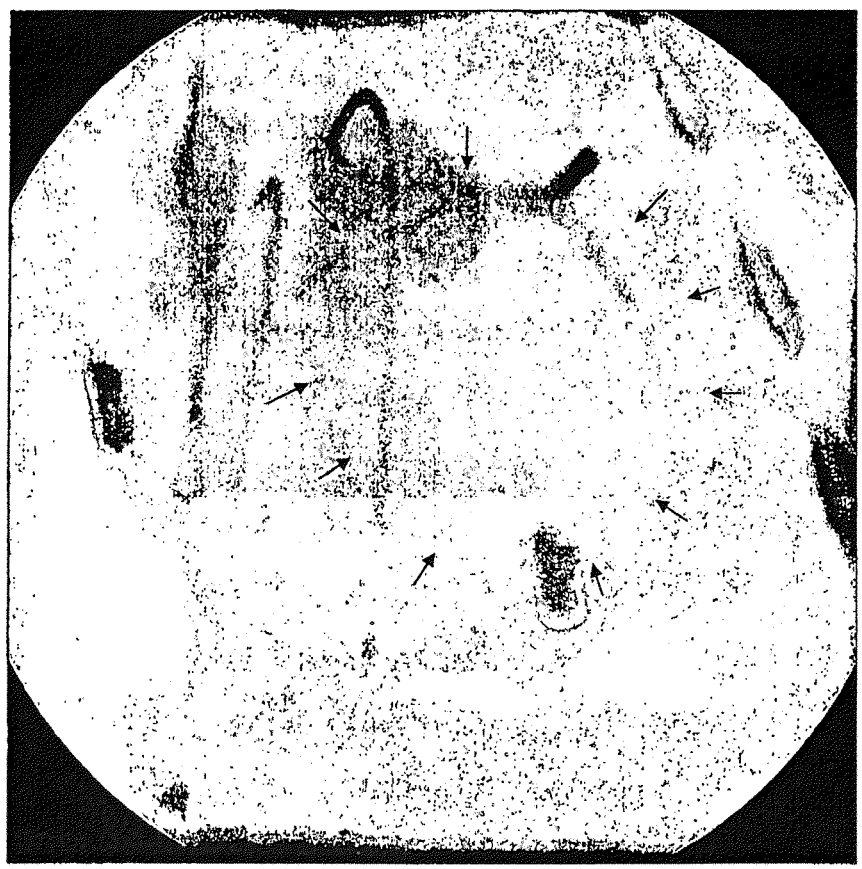
FIG. 6 is a digital image of a left coronary angiogram before tension is applied to a mitral annuloplasty wire in a pig. Arrows indicate the position of the annuloplasty wire that encircles the mitral annulus via the coronary sinus.

Annuloplasty Using Protective Device with Percutaneous Transluminal Coronary Angioplasty Wire for Cerclage This Example demonstrates the efficacy of one embodiment of the protective device in protecting the coronary artery from compression during trans-sinus annuloplasty. In this Example, the protective device was constructed of a stainless-steel hypotube (FIG. 5). A 57 kg Yucatan pig was anesthetized, and after obtaining vascular access in the right jugular vein, the femoral vein, and the femoral artery, an annuloplasty wire (0.014 conventional percutaneous transluminal coronary angioplasty (PTCA) wire) was positioned around the mitral annulus to form a cerclage using the method described herein in which tensioning material passes through the coronary sinus over a coronary artery. FIG. 6 shows the left coronary angiogram of the subject with the wire in position, but before tension was applied.

Figure 7:
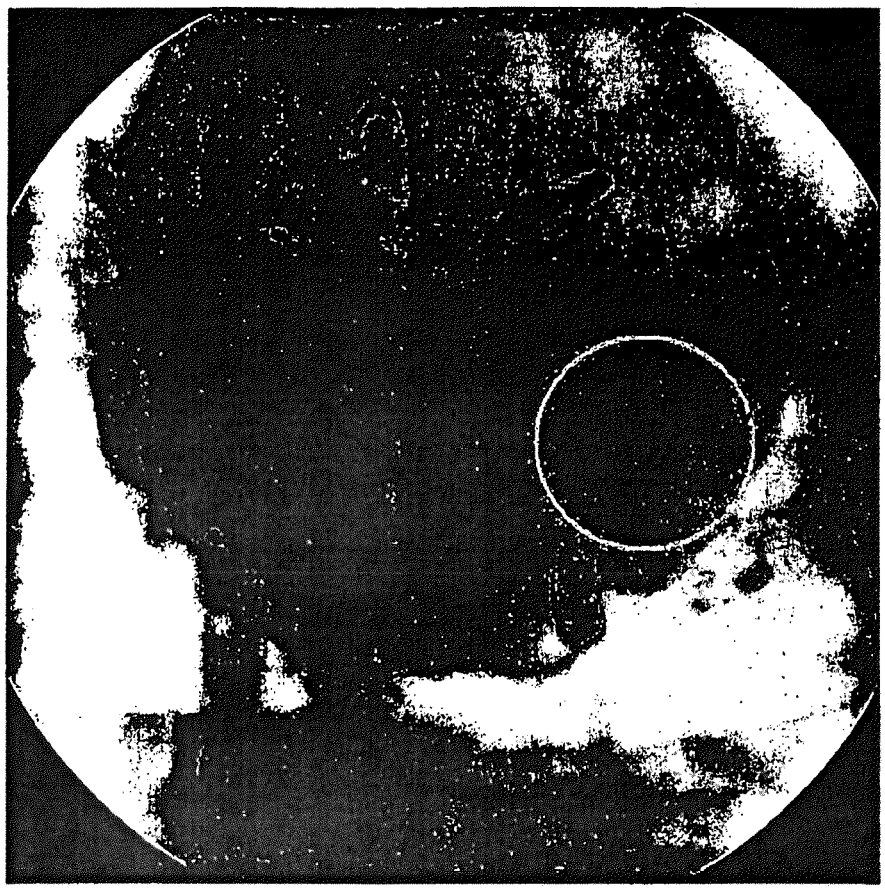
FIG. 7 is a digital image of a left coronary angiogram showing a part of the left circumflex artery that is severely pinched by an annuloplasty wire that encircles the mitral annulus via the coronary sinus in a pig.

After encircling the mitral annulus with the annuloplasty wire via the coronary sinus, tension was applied by traction on both ends of the externalized guide wire. When tension was applied to the wire, a focal segment of left circumflex artery was constricted where the coronary sinus lies superficial to the artery, so that the minimal lumen diameter of left circumflex artery decreased from 2.0 mm to 0.3 mm (FIG. 7).

Figure 8:
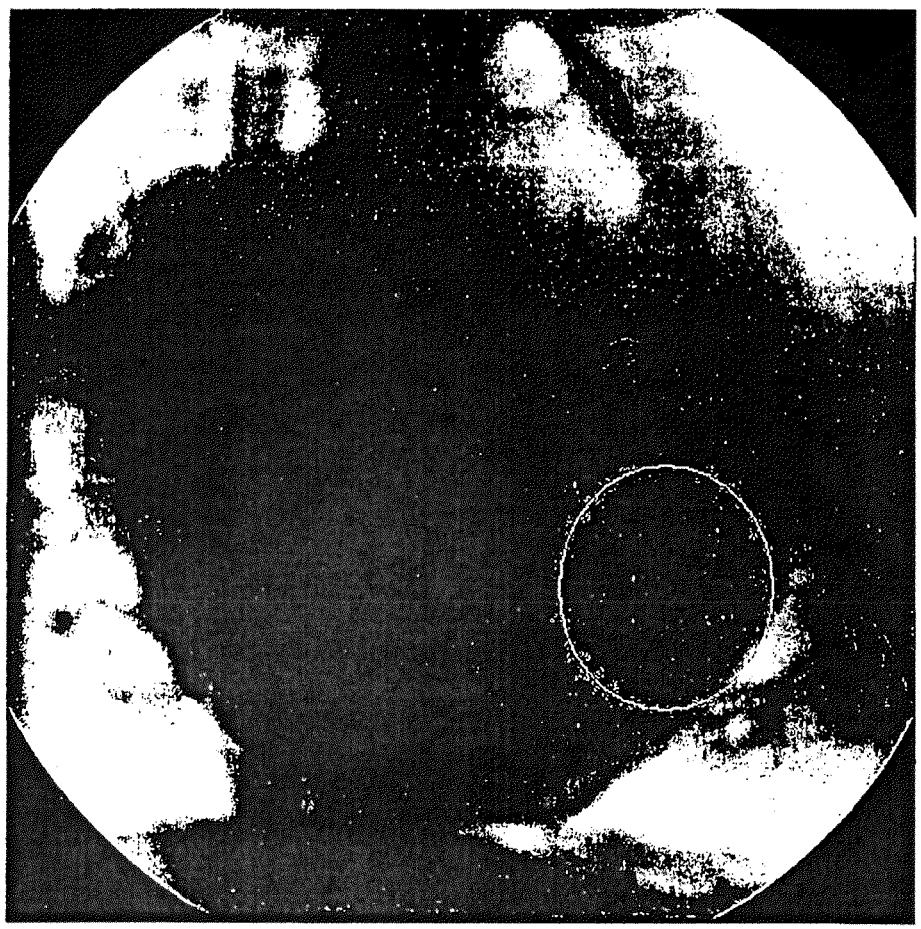
FIG. 8 is a digital image of a left coronary angiogram showing that the protective device protects the coronary artery from compression when tension is applied to a wire ligature that encircles the mitral annulus via the coronary sinus in a pig.

By contrast, when this same protocol was carried out a second time, but the protective device was positioned over the left circumflex artery branch, the coronary constriction was reduced to 1.5 mm of minimal luminal diameter of left circumflex artery when the same tension was applied to the wire (FIG. 8). Thus, the protective device protected the coronary artery from extrinsic compression during trans-sinus annuloplasty.

Example 2

Annuloplasty Using an Alternate Embodiment of the Protective Device

To quantify the protective ability of the device, the pressure in the left circumflex artery was measured using a conventional coronary pressure wire (Radi pressure wire). A 65 kg Yucatan pig was anesthetized, and after obtaining vascular access in the right jugular vein, the femoral vein, and the femoral artery, an annuloplasty wire (0.014 conventional PTCA wire) was positioned around the mitral annulus to form a cerclage essentially as described in Example 1. After placing the cerclage, but before tension was applied, the pressure wire was positioned at a site in the left circumflex artery that was distal to the point where the cerclage passed over the coronary artery. Distal coronary pressure was measured while tension was applied with and without the protective device in place over the left circumflex artery branch. The protective device ameliorated the reduction in distal coronary artery pressure caused by the tension in the cerclage.

Example 3

Annuloplasty Using a Third Embodiment of the Protective Device

Figure 9:
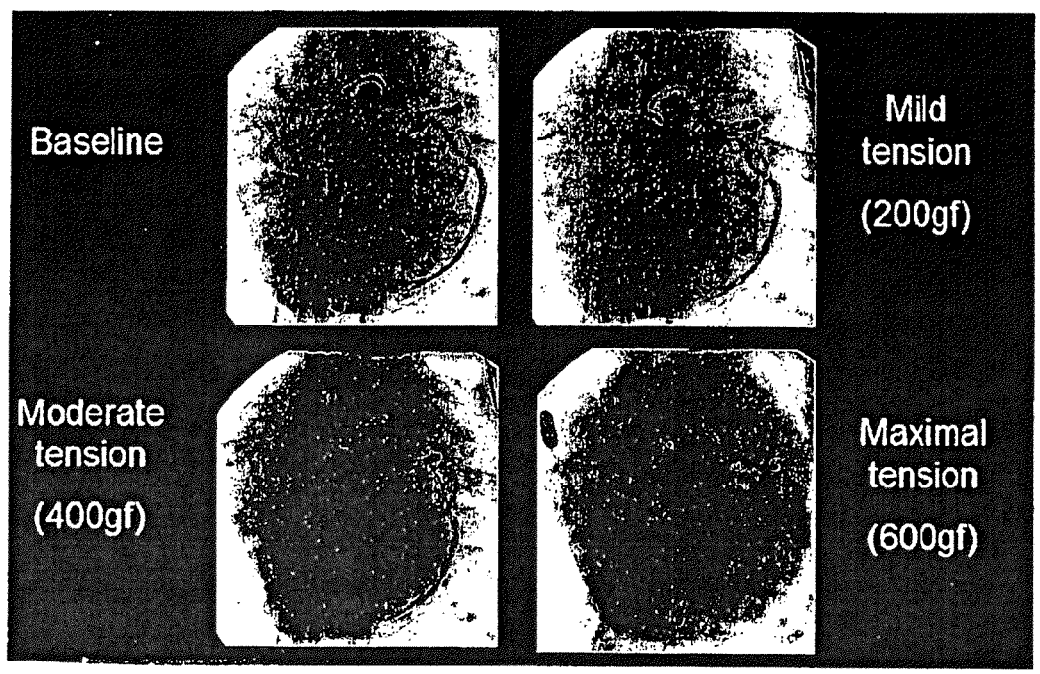
FIG. 9 is a series of four digital images of angiograms showing that the severity of compression of the left circumflex artery was positively correlated with the magnitude of tension applied to the cerclage ligature (without the protective device).

This Example demonstrates the efficacy of another alternate embodiment of the protective device. For this Example, the protective device was modified to augment the height of the central curve, and thereby further protect the coronary artery from compression during annuloplasty. A 74 kg Yucatan pig was anesthetized, and after obtaining vascular access in the right jugular vein, the femoral vein, and the femoral artery, an annuloplasty wire (0.014 conventional PTCA wire) was positioned around the mitral annulus to form a cerclage essentially as described in Example 1. After placing the cerclage, the end of cerclage wire from the right jugular vein was fixed and graded tensions of 0 grams, 200 grams, 400 grams and 600 grams were applied through the femoral end of a cerclage wire with and without the protective device in position over the left circumflex artery branch. FIG. 9 is a series of angiograms that show the effect on blood flow through the left circumflex artery when mild, moderate, and maximal tension was applied to the wire without the protective device in position.

Figure 10:
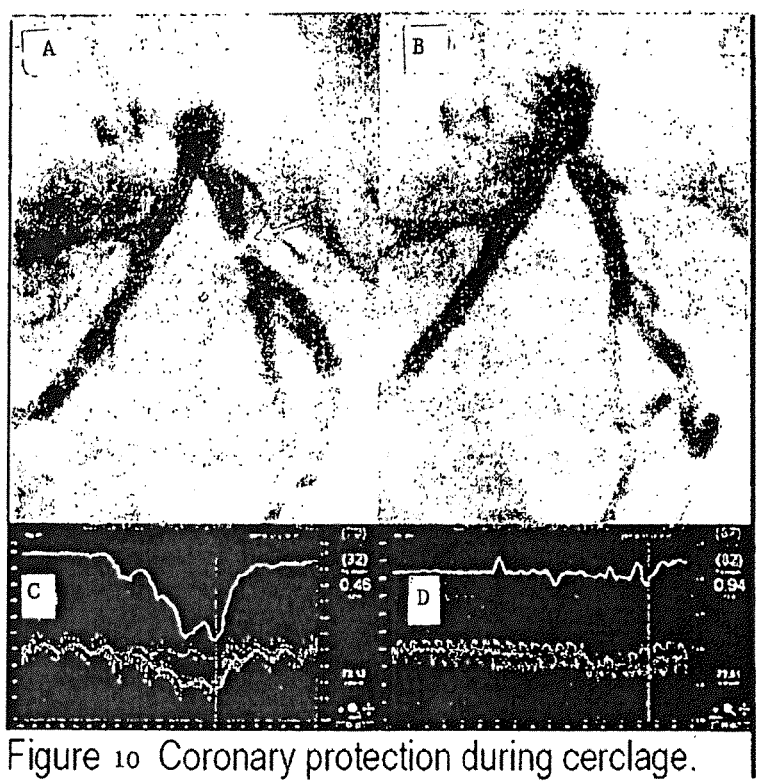
FIG. 10 shows the results of cerclage annuloplasty without (A, C) and with (B, D) the protective device. Panels A and B are digital images of coronary angiograms, while panels C and D are intracoronary pressure recordings.

The protective device was then positioned over the left circumflex artery branch and the same tensions were applied to the cerclage wire. While the phenomenon of coronary pinching became more pronounced as the tension increased, use of the protective device completely abated the drop in blood pressure that was observed when the protective device was not used (FIG. 10). The augmented height of the curve of the protective device in this embodiment improved the angiographic protection effect as compared to the protective devices of Examples 1 and 2.

Example 4

Use of the Protective Device with a Suture Cerclage

This Example demonstrates the efficacy of the protective device when used with a suture cerclage instead of a PTCA wire. A biocompatible suture material is a suitable cerclage ligature in many applications, however the metallic PTCA wire used in Examples 1-3 has different properties than a biocompatible suture. To determine whether the flexibility of the suture material affects the function of the protective device, the device was tested during a suture-based cerclage annuloplasty. A 55 kg Yorkshire pig was anesthetized, and after obtaining vascular access in the right jugular vein, the femoral vein, and the femoral artery, an annuloplasty wire (0.014 conventional PTCA wire) was positioned around the mitral annulus to form a cerclage essentially as described in Example 1. This procedure was then repeating using a conventional surgical suture that was made of non-absorbable black mono nylon with a thickness of 0.014 inches.

For this Example, the dimensions of the protective device were altered and the device was made from nitinol which is MRI-compatible. The width and height of the device were 0.536" and 0.1545" respectively, and the diameter of inner lumen and outer surface were 0.030" and 0.045" respectively. Tension was applied using the same method described in Examples 1-3. When tension was applied, a focal segment of proximal left circumflex artery was completely obstructed.

The protective device was positioned over the left circumflex artery branch via delivering catheter and tension was applied as described above. This embodiment of the protective device afforded complete protection (no coronary compression) at comparable annuloplasty cerclage tensions. Thus, this embodiment of the protection device completely prevents coronary artery compression when used in combination with a suture cerclage.

Example 5

Use of the Protection Device with Other Coronary Sinus Annuloplasty Techniques

The use of the protective device has been disclosed for use in a cerclage annuloplasty technique. However, the protective device can be used with any other annuloplasty device that extends even partially through the coronary sinus in a region that crosses an underlying coronary artery. For example, the protective device can be used to protect against compression of coronary arteries with any coronary sinus annuloplasty device, such as the coronary sinus device in U.S. Pat. No. 7,090,695 or the inflatable coronary sinus device shown in U.S. patent Ser. No. 10/787,574 (U.S. Patent Publication No. 2004/0254600). Although these devices are designed for endovascular delivery, the protection device disclosed herein can also be used with annuloplasty devices that are implanted using an open-chest surgical repair instead of a catheter based approach. The problem of coronary artery compression is also encountered with these devices, and the protective device disclosed herein may be used to avoid that problem. Hence the invention disclosed herein is not limited to a protective device for use with cerclage annuloplasty, nor is it limited to use of the device with catheter based delivery techniques.

When used with a coronary sinus annuloplasty implant of any kind, the protective device can be provided as an integral part of the implant or as a separate device suitable for placement between the implant and an underlying coronary artery to be protected. When provided as an integral part of the implant, the implant is positioned in the coronary sinus so that the arch of the support extends over the underlying coronary artery. In alternative embodiments the protection device is provided as a separate device that is advanced through the catheter system over the tensioning material until it is positioned over the coronary artery to be protected.

In view of the many possible embodiments to which the principles of this disclosure may be applied, it should be recognized that the illustrated embodiments are only preferred examples of the disclosure and should not be taken as limiting the scope of the disclosure. We therefore claim all that comes within the scope and spirit of the following claims.

We claim:

1. A protection device for protecting a coronary artery from compression during catheter-based mitral annuloplasty, the device comprising:

a surgically sterile protective member comprising a proximal free end, a distal free end, and an arch centrally positioned between the proximal and distal free ends, the protective member configured to pass through a transvascular catheter and fit within a coronary sinus of a heart at a location where the coronary sinus passes over a coronary artery of the heart, and the protective member including a passageway extending from the proximal free end to the distal free end of the protective member;

a circumferential annuloplasty tension element extending through the passageway of the protective member and configured to extend entirely around the mitral valve and be placed under tension;

wherein the arch of the protective member has sufficient rigidity and dimensions to inhibit application of pressure to the coronary artery when the protective member is positioned at said location with the circumferential annuloplasty tension element extending entirely around the mitral valve under tension, causing the arch of the protective member to orient away from the coronary artery, thereby protecting the coronary artery from compression.

2. The device of claim 1, wherein the proximal and distal free ends of the protective member form stabilizers that are configured to generally conform to a wall of the coronary sinus and retain the arch in position bridging over the coronary artery.

3. The device of claim 1, wherein the arch of the protective member bridges a linear distance at its base of about 0.5 inches to about 0.6 inches.

4. The device of claim 1, wherein the arch of the protective member is about 0.15 inches to about 0.16 inches high.

5. A protection device for protecting a coronary artery of a heart from compression during catheter-based mitral annuloplasty in which a circumferential annuloplasty tension element extends at least partially through a coronary sinus of the heart over an outer surface of the coronary artery, the device comprising:

a protective member comprising a proximal free end and a distal free end and an arch centrally located between the proximal and distal free ends, the protective member configured to pass through a transvascular catheter and fit within the coronary sinus at a location where the coronary sinus passes over the coronary artery, the protective member being configured to be positioned along a circumferential annuloplasty tension element that extends entirely around the mitral valve;

wherein the arch of the protective member has sufficient rigidity and dimensions to inhibit application of pressure by the circumferential annuloplasty tension element to the underlying coronary artery when the protective member is positioned in the coronary sinus over the coronary artery and the circumferential annuloplasty tension element is placed under tension during mitral annuloplasty, wherein tension from the tension element causes the centrally located arch of the protective member to orient away from the underlying coronary artery when the arch is positioned over the coronary artery such that the arch bridges entirely across the coronary artery, thereby protecting the underlying coronary artery from compression;

wherein proximal and distal free ends of the protective member are collinear with each other and extend in opposite directions from the arch when the protective member is unstressed, wherein the arch has a length extending from the proximal free end to the distal free end and a width perpendicular to the length, wherein the width is substantially uniform along the length.

6. The device of claim 5, wherein the proximal and distal free ends of the protective member form stabilizers that are configured to generally conform to a wall of the coronary sinus and retain the arch in position bridging over the coronary artery.

7. The device of claim 5, wherein the arch of the protective member bridges a linear distance at its base of about 0.5 inches to about 0.6 inches.

8. The device of claim 5, wherein the arch of the protective member is about 0.15 inches to about 0.16 inches high.

9. The device of claim 5, wherein the protective member comprises a shape memory material.

10. A protection device for protecting a coronary artery of a heart from compression during catheter-based mitral annuloplasty in which a circumferential annuloplasty tension element extends at least partially through a coronary sinus of the heart over an outer surface of the coronary artery, the device comprising:
    a surgically sterile tubular protective member comprising a proximal free end and a distal free end and an arch centrally located between the proximal and distal free ends, the arch having a substantially uniform diameter along its length, the protective member configured to pass through a transvascular catheter and fit within the coronary sinus at a location where the coronary sinus passes over the coronary artery, the protective member having an enclosed passageway extending from the proximal free end to the distal free end of the protective member, and the protective member being configured to receive the circumferential annuloplasty tension element through the passageway;
    wherein the arch of the protective member has sufficient rigidity and dimensions to inhibit application of pressure to the underlying coronary artery when the protective member is positioned in the coronary sinus over the coronary artery, and when the circumferential annuloplasty tension element is positioned through the passageway and placed under tension during mitral annuloplasty causing the centrally located arch of the protective member to orient away from the underlying coronary artery, thereby protecting the underlying coronary artery from compression; and
    wherein the arch bridges a maximum linear distance at its base of about 0.5 inches to about 0.6 inches.

11. The device of claim 10, wherein the proximal and distal free ends form stabilizers that are configured to generally conform to a wall of the coronary sinus and retain the protection device in position over the coronary artery.

12. The device of claim 11, wherein the stabilizers are stabilizing feet.

13. The device of claim 12, wherein the device comprises a shape memory material.

14. The device of claim 13, wherein the tubular protective member has an outer diameter from about 0.04 to about 0.05 inches, and an inner diameter from about 0.025 inches to about 0.035 inches along its entire length.

15. The device of claim 14, wherein a distance between the proximal end and the distal end of the tubular protective member is about 0.536 inches, the height of the arch is about 0.1545 inches, the outer diameter of the protective member is about 0.045 inches, and the inner diameter of the protective member is about 0.030 inches.

16. The device of claim 10, wherein the arch bridges a maximum linear distance at its base of from about 0.52 inches to about 0.55 inches.

17. The device of claim 10, wherein the arch is about 0.15 inches to about 0.16 inches high.

18. The device of claim 10, wherein the tubular protective member has an outer diameter from about 0.04 to about 0.05 inches, and an inner diameter from about 0.025 inches to about 0.035 inches along its entire length.

19. The device of claim 18, wherein the outer diameter of the tubular protective member is about 0.045 inches along its entire length, and the inner diameter is from about 0.025 inches to about 0.035 inches along its entire length.

20. The device of claim 18, wherein a distance between the proximal end and the distal end of the tubular protective member is about 0.536 inches, the height of the arch is about 0.1545 inches, the outer diameter of the protective member is about 0.045 inches, and the inner diameter of the protective member is about 0.030 inches.

21. The device of claim 10, wherein the device comprises a shape memory material.

* * * * *